(12) United States Patent
Seong et al.

(10) Patent No.: US 8,591,806 B2
(45) Date of Patent: Nov. 26, 2013

(54) ADVANCED OXIDATION SYSTEM FOR TREATMENT OF OFFENSIVE ODORS AND TOXIC SUBSTANCES OF FOUNDRY WASTE AND TREATMENT METHOD USING THE SAME

(75) Inventors: Kwang Mo Seong, Gyeonggi-do (KR); Whee Moon Choi, Gyeonggi-do (KR)

(73) Assignee: Hyundai Motor Company, Seoul (KR)

( * ) Notice: Subject to any disclaimer, the term of this patent is extended or adjusted under 35 U.S.C. 154(b) by 127 days.

(21) Appl. No.: 13/232,363

(22) Filed: Sep. 14, 2011

(65) Prior Publication Data
US 2013/0004365 A1 Jan. 3, 2013

(30) Foreign Application Priority Data
Jun. 30, 2011 (KR) .................. 10-2011-0065196

(51) Int. Cl.
*A61L 9/14* (2006.01)
(52) U.S. Cl.
USPC .......................................... 422/5; 250/492.1
(58) Field of Classification Search
USPC ............... 422/5; 250/492.1; 164/412
See application file for complete search history.

(56) References Cited

U.S. PATENT DOCUMENTS 4,377,459 A * 3/1983 Parker ........................ 525/239
5,477,909 A 12/1995 Becker
6,476,287 B1 11/2002 Hale, III et al.

FOREIGN PATENT DOCUMENTS

KR  10-0393344  3/2002
KR  10-0558314  9/2005

* cited by examiner

*Primary Examiner* — Sean E Conley
(74) *Attorney, Agent, or Firm* — Edwards Wildman Palmer LLP; Peter F. Corless (57) ABSTRACT

The present invention provides an advanced oxidation system for the treatment of offensive odors and toxic substances of foundry waste, e.g., sand, and a treatment method using the same, which can effectively remove offensive odors and toxic substances produced during a sand reclamation process for reclamation of foundry waste. For this purpose, an advanced oxidation system for the treatment of offensive odors and toxic substances of foundry waste by implementing a spray device for spraying a diluted solution of hydrogen peroxide onto foundry waste; a stirring device for mixing the foundry waste with the diluted solution of hydrogen peroxide sprayed thereto; an ultraviolet irradiation device for activating the hydrogen peroxide mixed with the foundry waste to produce radicals; and a local exhaust system for collecting dust generated when the foundry waste is mixed with the hydrogen peroxide by the stirring device.

5 Claims, 6 Drawing Sheets

FIG.1

PRIOR ART

ADVANCED OXIDATION SYSTEM FOR TREATMENT OF OFFENSIVE ODORS AND TOXIC SUBSTANCES OF FOUNDRY WASTE AND TREATMENT METHOD USING THE SAME

CROSS-REFERENCE TO RELATED APPLICATION

This application claims under 35 U.S.C. §119(a) the benefit of Korean Patent Application No. 10-2011-0065196 filed Jun. 30, 2011, the entire contents of which are incorporated herein by reference.

BACKGROUND (a) Technical Field

The present invention relates to the treatment of offensive odors and toxic substances of foundry waste. More particularly, it relates to an advanced oxidation system for the treatment of offensive odors and toxic substances of waste foundry sand and a treatment method using the same, which can effectively remove offensive odors and toxic substances produced during a sand reclamation process for reclamation of waste foundry sand.

(b) Background Art

The improvement of the environmental standards in recent decades has increased people's interest in the industrial community's effect on the environment. As cities expand, large-scale residential areas have become established around industrial complexes previously located on the periphery of the cities. As a result, there has been an increase in the number of civil complaints from residents of the surrounding communities, especially regarding offensive odors and the like.

Accordingly, local government has imposed strict regulations on offensive odors and toxic substances, which typically require a counter-plan for reducing the emission of offensive odors and toxic substances which impact on the environment surrounding these factories. In particular, foundries have been affected by these laws and regulations because they typically emit toxic substances such as phenols, amines, etc., whose odor can be detected even at a very low concentrations and is therefore subject to the regulations. For example, phenols and amines are generated mainly by pyrolysis of phenol resin as a bonding agent and amine as a curing agent or hexamine as a curing accelerator used for sand bonding by pouring.

In the foundry, the offensive odors are emitted during the core manufacturing process, a pouring/cooling process, a de-molding process, and a sand reclamation process. Among these four processes, a wet suppression system is provided at the end of each of the core manufacturing process and the pouring/cooling process to minimize the emission of offensive odors and toxic substances. In the de-molding process, a wet suppression system for removing dust is converted into a dry suppression system to treat the dust, offensive orders, and toxic substances. However, in the sand reclamation process, the transfer distance using a conveyer is too long to install appropriate local exhaust system and air suppression system.

The sand reclamation process typically includes a crushing process which crushes the waste foundry sand into sand granules, a transfer process that transfers the sand granules using a conveyor, a sieving process that removes the remaining waste foundry sand, and a mixing process that mixes the waste foundry sand granules, new sand, clay, sea coal, and water. In all the unit processes, offensive odors and toxic substances are emitted from the waste foundry sand and thus, dispersed and scattered over a workplace and the neighboring residential area (i.e., the civil complaint area).

Figure 1:
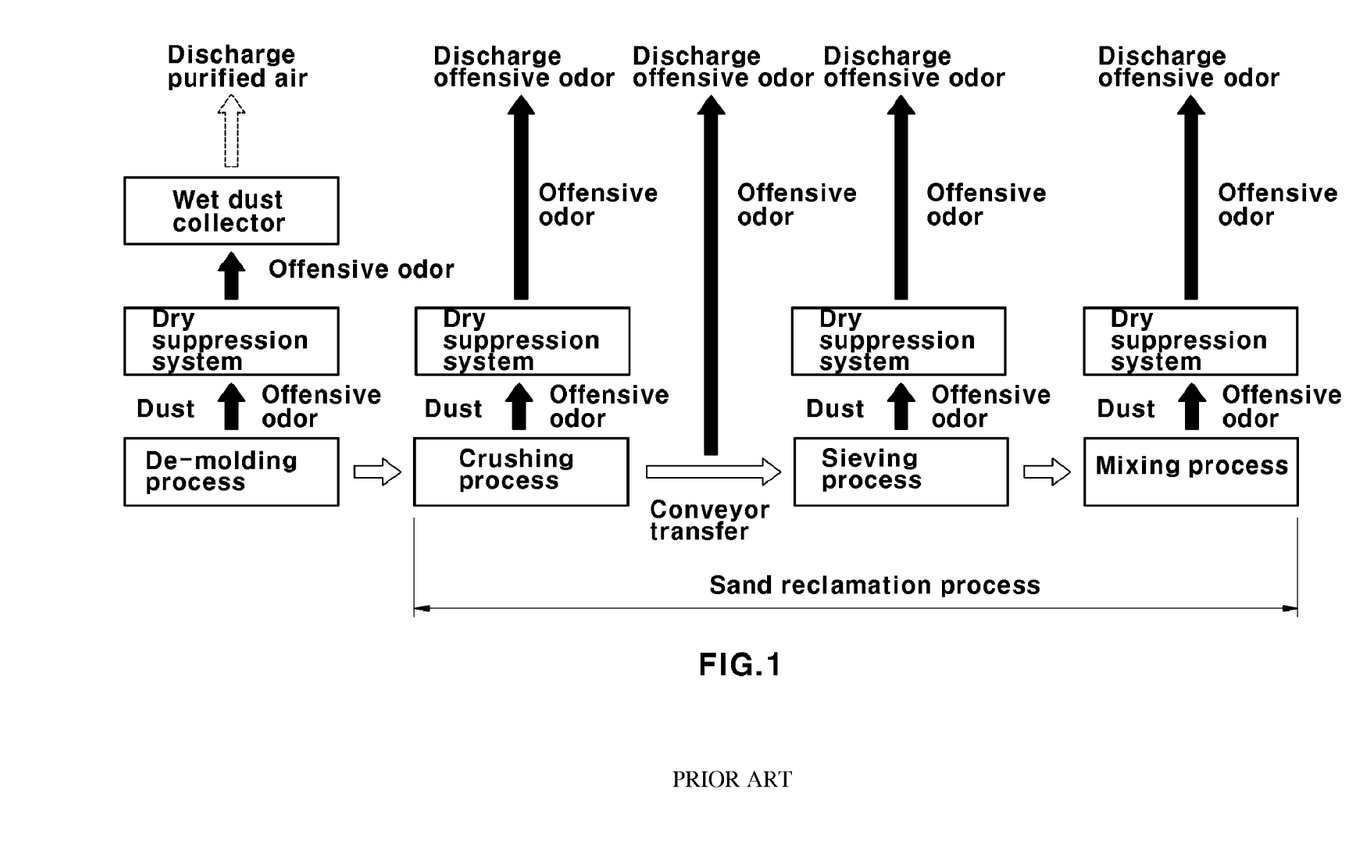
FIG. 1 is diagram showing a suppression system applied to a conventional sand reclamation process and each unit process thereof.

As shown in FIG. 1, in the conventional sand reclamation process, the crushing process, the sieving process, and the mixing process are not provided with a separate system for the treatment of offensive odors and toxic substances other than a dust treatment system (i.e., dry suppression system), and thus only the dust is removed. However, the offensive odors and toxic substances are still emitted to the air. More specifically, the transfer process, which uses the conveyor, is not provided with a local exhaust system and an air suppression system, and thus the dust, offensive orders, and toxic substances are scattered over the workplace and dispersed into the outside of the foundry during the transfer process.

In order to reduce the emission of offensive odors and toxic substances during the sand reclamation process, it would be beneficial to install and manage a wet suppression system in each process. However, when the wet suppression system is installed in each of the four processes, the initial investment costs are very high, and further the annual operating expenses are significantly increased. As such, to install and manage the wet suppression system in the sand reclamation system, the investment costs would be extensive, and when there is not sufficient space the foundry, it is very difficult to install the wet suppression system.

The above information disclosed in this Background section is only for enhancement of understanding of the background of the invention and therefore it may contain information that does not form the prior art that is already known in this country to a person of ordinary skill in the art.

SUMMARY OF THE DISCLOSURE

The present invention provides an advanced oxidation system for the treatment of offensive odors and toxic substances of foundry waste and a treatment method using the same, which can oxidatively decompose of offensive odors and toxic substances produced during a transfer process of a sand reclamation process for reclamation of foundry waste.

In one aspect, the present invention provides an advanced oxidation system for the treatment of offensive odors and toxic substances of foundry waste, the system comprising: a spray device for spraying a diluted solution of hydrogen peroxide onto foundry waste; a stirring device for mixing the foundry waste with the diluted solution of hydrogen peroxide sprayed thereto; an ultraviolet irradiation device for activating the hydrogen peroxide mixed with the foundry waste to produce radicals; and a local exhaust system for collecting dust generated when the foundry waste is mixed with the hydrogen peroxide by the stirring device.

In an exemplary embodiment, the ultraviolet irradiation device may comprise a plurality of ultraviolet lamps for irradiating ultraviolet rays over a mixing vessel of the stirring device and a reflecting means or device for concentrating the ultraviolet rays irradiated from the ultraviolet lamps on the mixing vessel of the stirring device.

In another exemplary embodiment, the reflecting means may be configured to surround the top and side or sides of the ultraviolet lamps. Additionally, the local exhaust system may comprise a connecting duct connected to a dry suppression system to transfer the collected dust.

In another aspect, the present invention provides a method for the treatment of offensive odors and toxic substances of foundry waste using an advanced oxidation system, the method comprising the steps of: spraying a diluted solution of hydrogen peroxide onto foundry waste; mixing the foundry waste with the diluted solution of hydrogen peroxide sprayed thereto; irradiating ultraviolet rays onto the foundry waste mixed with the diluted solution of hydrogen peroxide; and collecting dust generated when the foundry waste is mixed with the hydrogen peroxide.

In an exemplary embodiment, in the step of irradiating the ultraviolet rays, ultraviolet rays of more than 2 W per 1 kg foundry waste are irradiated onto the foundry waste for more than 3 minutes.

Other aspects and exemplary embodiments of the invention are discussed infra.

BRIEF DESCRIPTION OF THE DRAWINGS

The above and other features of the present invention will now be described in detail with reference to certain exemplary embodiments thereof illustrated the accompanying drawings which are given hereinbelow by way of illustration only, and thus are not limitative of the present invention, and wherein.

Reference numerals set forth in the Drawings includes reference to the following elements as further discussed below:

10: spray device
11: hydrogen peroxide tank
12: hydrogen peroxide supply line
13: industrial water supply line
14: bubbling device
15: air supply line
16: blower
17: mist transfer duct
18: hood
19: reaction vessel
20: stirring device
21: conveyor
22: mixing vessel
23: mixing means
30: ultraviolet irradiation device
31: ultraviolet lamp
32: reflecting means
40: local exhaust system
41: collecting hood
42: connecting duct
43: suction device (or blower)

It should be understood that the appended drawings are not necessarily to scale, presenting a somewhat simplified representation of various exemplary features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

Hereinafter reference will now be made in detail to various embodiments of the present invention, examples of which are illustrated in the accompanying drawings and described below. While the invention will be described in conjunction with exemplary embodiments, it will be understood that present description is not intended to limit the invention to those exemplary embodiments. On the contrary, the invention is intended to cover not only the exemplary embodiments, but also various alternatives, modifications, equivalents and other embodiments, which may be included within the spirit and scope of the invention as defined by the appended claims.

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, plug-in hybrid electric vehicles, hydrogen-powered vehicles and other alternative fuel vehicles (e.g., fuels derived from resources other than petroleum). As referred to herein, a hybrid vehicle is a vehicle that has two or more sources of power, for example both gasoline-powered and electric-powered vehicles.

The present invention provides an advanced oxidation system for the treatment of offensive odors and toxic substances produced during a transfer process of a sand reclamation process for reclamation of foundry waste and a method for the treatment of offensive odors and toxic substances using the same, which can oxidatively decompose offensive odors and toxic substances produced from the foundry waste, e.g., sand during the sand reclamation process, thereby improving workplace environments and resolving civil complaints from neighboring residential areas.

Figure 2:
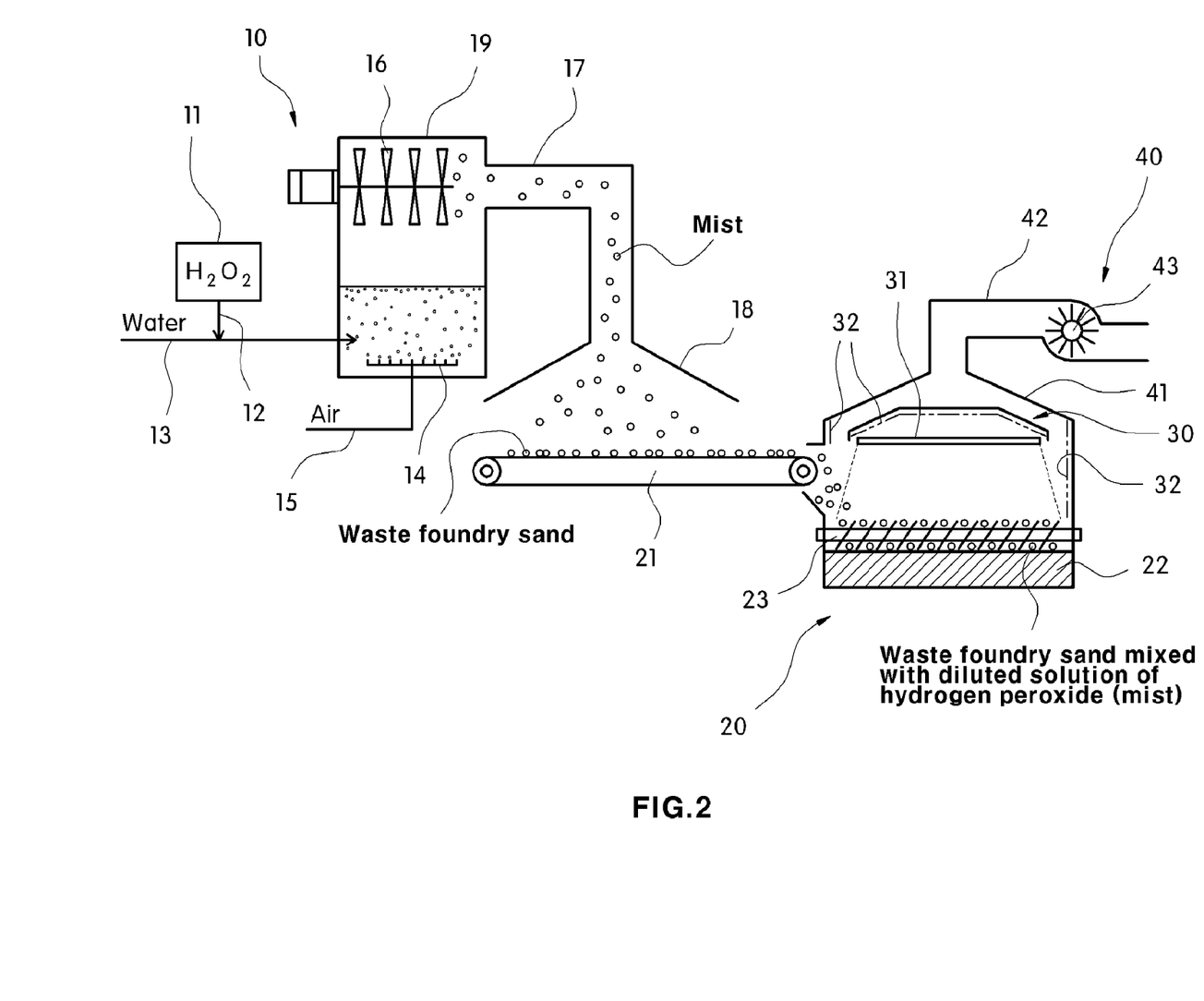
FIG. 2 is a diagram showing the configuration of an advanced oxidation system for the treatment of offensive odors and toxic substances of foundry waste in accordance with an exemplary embodiment of the present invention.

To this end, as shown in FIG. 2, the advanced oxidation system in accordance with a exemplary embodiment of the present invention generally includes a spray device 10 for spraying a diluted solution of hydrogen peroxide onto foundry waste, a stirring device 20 for mixing the foundry waste with the diluted solution of hydrogen peroxide sprayed thereto, an ultraviolet irradiation device 30 for activating the hydrogen peroxide mixed with the foundry waste to produce radicals (Off), and a local exhaust system 40 for collecting dust generated when the foundry waste is mixed with the hydrogen peroxide by the stirring device 20.

The spray device 10 has a hydrogen peroxide tank 11 for storing hydrogen peroxide, a hydrogen peroxide supply line 12 for supplying the hydrogen peroxide, an industrial water supply line 13 for supplying industrial water, a reaction vessel 19 to which a mixture of the hydrogen peroxide and the industrial water, e.g., a diluted solution of hydrogen peroxide, is supplied, a bubbling device 14 for generating a mist by bubbling the diluted solution of hydrogen peroxide in the reaction vessel 19, and a blower 16 for blowing the mist in the reaction vessel 19.

A mist transfer duct 17 for guiding the mist discharged from the reaction vessel 19 is connected to the reaction vessel 19, and a hood 18 for covering a wider cross-sectional area (in which the foundry waste is placed on a conveyor belt and transferred thereby) of a conveyor 21 is provided at the end of the mist transfer duct 17. Here, the conveyor 21 may be a transfer conveyor for transferring the foundry waste during the sand reclamation process. The bubbling device 14 is mounted at the bottom of the reaction vessel 19 to bubble the diluted solution of hydrogen peroxide using air supplied through an air supply line 15 provided on the outside of the reaction vessel 19. The blower 16 is mounted on one of the side walls of the reaction vessel 19 and driven by a motor configured to blow the generated mist at the top of the diluted solution of hydrogen peroxide. The hydrogen peroxide supplied through the hydrogen peroxide supply line 12 and the industrial water supplied through the industrial water supply line 13 are mixed together to form the diluted solution of hydrogen peroxide during transfer.

The spray device 10, configured as described above, supplies the mist generated by the bubbling device 14 in the reaction vessel 19 to the foundry waste on the conveyor 21 using the blower 16. Here, in order to increase the contact efficiency between the diluted solution of hydrogen peroxide and the foundry waste and prevent unnecessary waste of the diluted solution of hydrogen peroxide, it is beneficial to generate and spray the mist as fine as possible.

The stirring device 20 may include a mixing vessel 22 for receiving the foundry waste (e.g., mixed with the diluted solution of hydrogen peroxide) transferred by the conveyor 21 and a mixing means or device 23 for uniformly mixing the mixture of the foundry waste received in the mixing vessel 22 and the diluted solution of hydrogen peroxide. Here, the mixing means/device 23 may be configured with a screw mounted in the mixing vessel 22. The stirring device 20 increases the contact time between the diluted solution of hydrogen peroxide and the foundry waste and allows the ultraviolet rays to be uniformly irradiated onto the mixture of the foundry waste and the diluted solution of hydrogen peroxide, thereby accelerating the oxidative decomposition of offensive odors and toxic substances.

Figure 3:
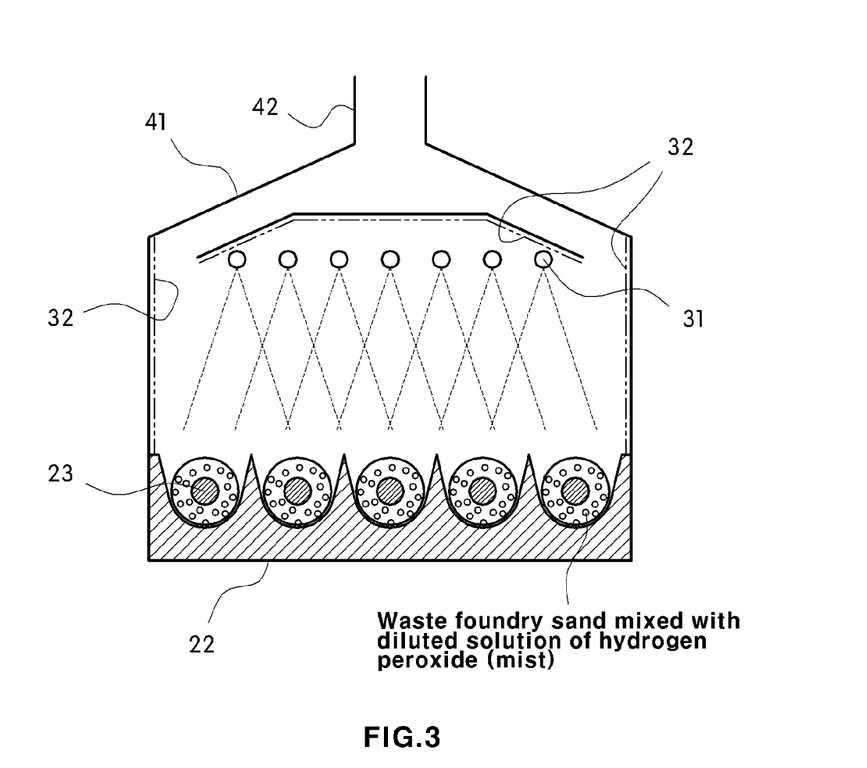
FIG. 3 is an enlarged view of a principal portion of FIG. 2, viewed from the side.

The ultraviolet irradiation device 30 may include a plurality of ultraviolet lamps 31 for irradiating ultraviolet rays over the mixing vessel 22 of the stirring device 20 and a reflecting means or device 32 for concentrating the ultraviolet rays irradiated from the ultraviolet lamps 31 on the mixing vessel 22 of the stirring device 20. The plurality of ultraviolet lamps 31 may be disposed in consideration of the top cross-sectional area of the mixing vessel 22 and the irradiation angle of the lamps 31 and may be disposed in parallel to each other in one direction as shown in FIG. 3. The ultraviolet lamps 31 may be configured to irradiate ultraviolet rays of more than 2 W per 1 kg foundry waste for more than 3 minutes, where the wavelength of the ultraviolet rays is about 250 to 260 nm The ultraviolet irradiation device 30, configured as described above, serves to activate the hydrogen peroxide sprayed onto the foundry waste to produce radicals ($OH^-$), thereby oxidatively decomposing the offensive odors and toxic substances.

Preferably, the reflecting means/device 32 is configured to surround the top and side of the ultraviolet lamps 31 such that the ultraviolet rays irradiated over the mixing vessel 22 can be more effectively utilized. In particular, as shown in FIG. 3, the reflecting means/device 32 provided at the side of the mixing vessel 22 is configured to connect the bottom of a collecting hood 41 and the top of the mixing vessel 22 to prevent the ultraviolet rays from leaking. Moreover, the edge of the reflecting means 32 provided at the top of the mixing vessel 22 may be bent downward such that the reflected ultraviolet rays are irradiated over the mixing vessel 22.

Figure 4:
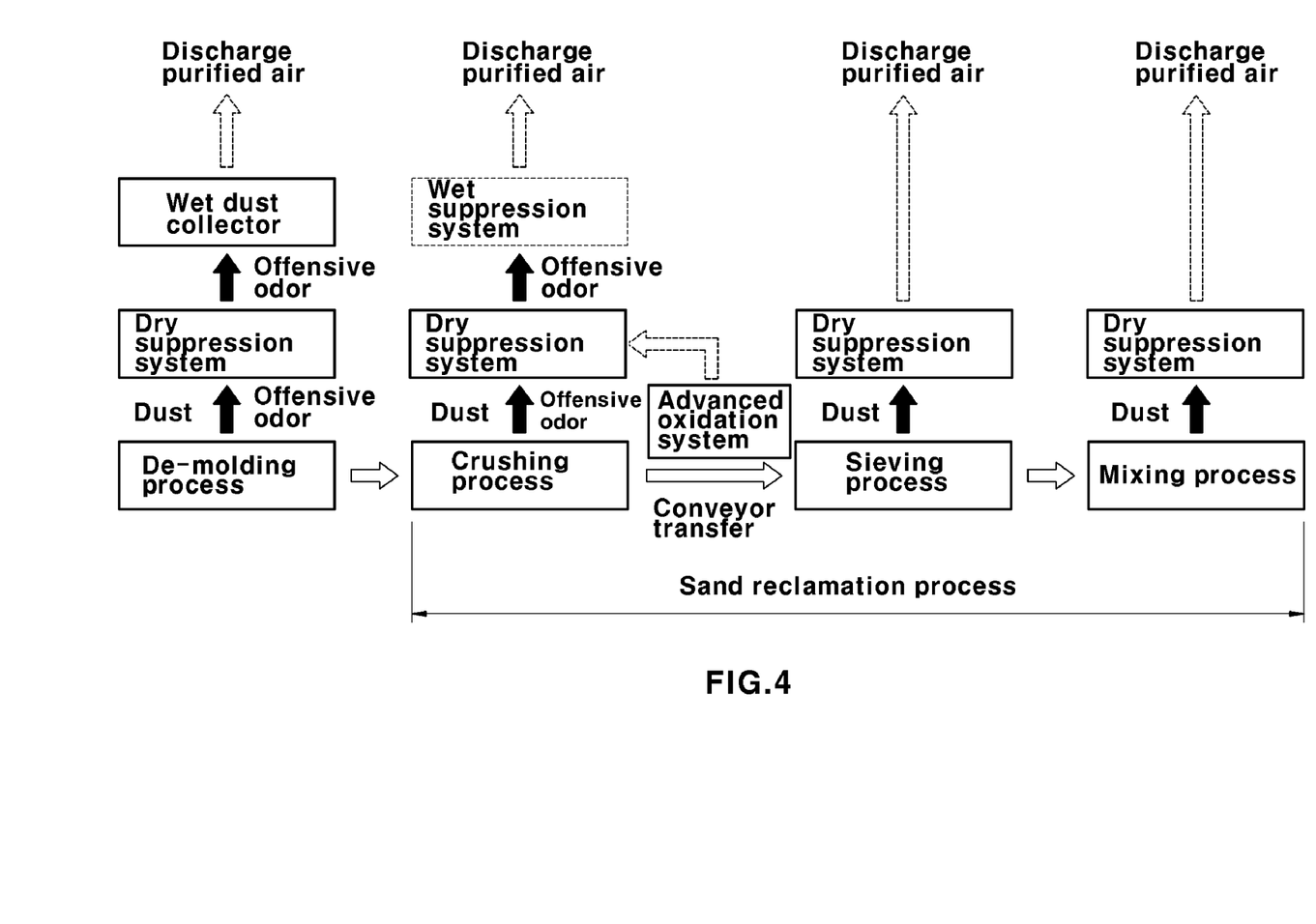
FIG. 4 is a schematic diagram showing a sand reclamation process employing an advanced oxidation system in accordance with the present invention.

Finally, the local exhaust system 40 may include a suction device 43 for collecting dust generated by the mixing process of the stirring device 20 and a connecting duct 42 for transferring the dust collected by the suction device 43. The suction device 43 is provided on one side of the connecting duct 42 to suction the collected dust through the connecting duct 42, and one end of the connecting duct 42 is connected to a dry suppression system to transfer the collected dust to the dry suppression system. Moreover, the other end of the connecting duct 42 is connected to the funnel-shaped collecting hood 41, and the collecting hood 41 is configured to cover the wide top surface of the mixing vessel 22. Here, the dry suppression system serves to remove the dust generated during a crushing process of the sand reclamation process and, as shown in FIG. 4, removes the dust transferred from the connecting duct 42. The local exhaust system 40, configured as described above, serves to collect the oxidized by-products together with the dust generated during the treatment of offensive odors and toxic substances, thereby preventing contamination of the workplace.

Moreover, as shown in FIG. 4, a wet suppression system is connected to the dry suppression system for removing the dust generated during the crushing process to remove the offensive odors and toxic substances produced during the sand reclamation process, thereby discharging purified air. As such, when the advanced oxidation system of the present invention is applied to the sand reclamation system, the wet suppression system is provided only to the crushing process, and not all the unit processes of the sand reclamation process, to discharge purified air from which the offensive odors and toxic substances have been removed therefrom, thereby improving the workplace environment and the neighboring residential area.

Next, the method for the treatment of offensive odors and toxic substances using the advanced oxidation system in accordance with another exemplary embodiment of the present invention will be described.

First, the industrial water supplied through the industrial water supply line 13 and hydrogen peroxide supplied through the hydrogen peroxide supply line 12 is mixed together to form a diluted solution of hydrogen peroxide. The diluted solution of hydrogen peroxide is fed into the reaction vessel 19 and a mist is generated by the operation of the bubbling device 14. The mist is supplied to the conveyor 21 by the blower 16 and sprayed onto the foundry waste placed on the conveyor 21.

The foundry waste mixed with the mist, i.e., the diluted solution of hydrogen peroxide, is transferred to the mixing vessel 22 of the stirring device 20 by the operation of the conveyor 21, in which the foundry waste and the diluted solution of hydrogen peroxide are uniformly mixed together by the mixing means 23. Here, the hydrogen peroxide is activated by the ultraviolet rays irradiated from the ultraviolet lamps 31 to produce radicals. These produced radicals remove the offensive odors and toxic substances from the foundry waste by oxidative decomposition. Preferably, the suction device 43 of the local exhaust system 40 is operated at this time to collect the dust generated when the foundry waste is mixed with the hydrogen peroxide by the stirring device 20, thereby preventing the dust from being scattered over the workplace.

The thus treated foundry waste reduces or eliminates the generation of offensive odors and toxic substances during the subsequent sieving and mixing processes, and thus, as shown in FIG. 4, it is possible to prevent the emission of offensive odors and toxic substances after the transfer process. Moreover, the dust collected by the local exhaust system 40 is transferred to the dry suppression system of the crushing process and then treated together with the dust generated during the crushing process. Since the air current of the suction device 43 (or blower) is formed in the sectional direction generated by the suction device 43, the dust and the decomposition by-products such as offensive odors and toxic substances are collected along the air current, and the collected pollutants can be transferred to the dry suppression system along the connecting duct 42.

Advantageously, the offensive odors and toxic substances, produced from the foundry waste during the transfer process of the sand reclamation process, are oxidatively decomposed, and the dust and the decomposition by-products, such as offensive odors and toxic substances, emitted during the process are collected and treated, thereby improving the workplace environment and the environment of neighboring residential area. Moreover, a separate suppression system is not required, and thus the installation and maintenance costs can be saved. Further, according to the present invention, since the pollutants adhering to the foundry waste can be continuously removed, it is possible to increase the number of reuse times, thereby reducing the cost for purchasing new foundry sand.

Figure 5:
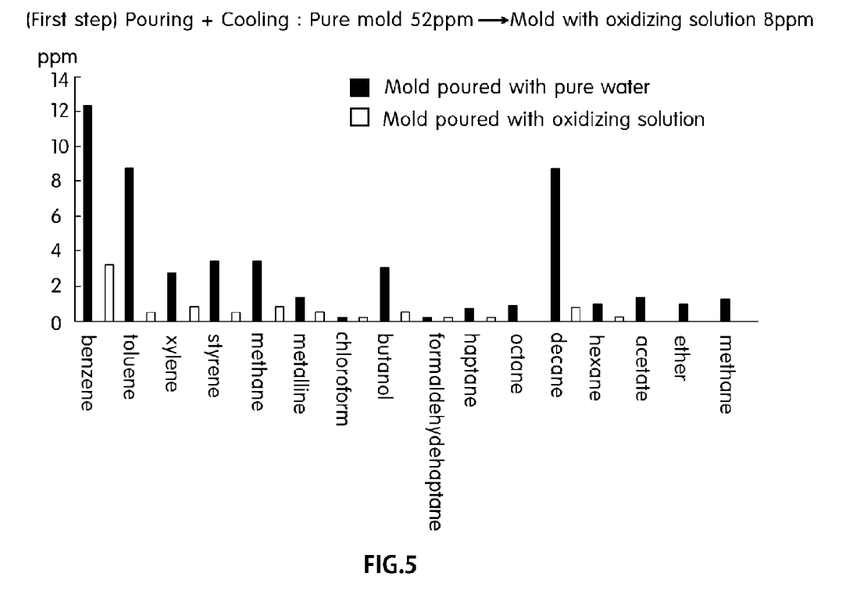
FIGS. 5 and 6 are diagrams showing the reduction of toxic substances in each process evaluated using a mold prepared by recycling foundry waste treated by advanced oxidation in accordance with the present invention.
Figure 6:
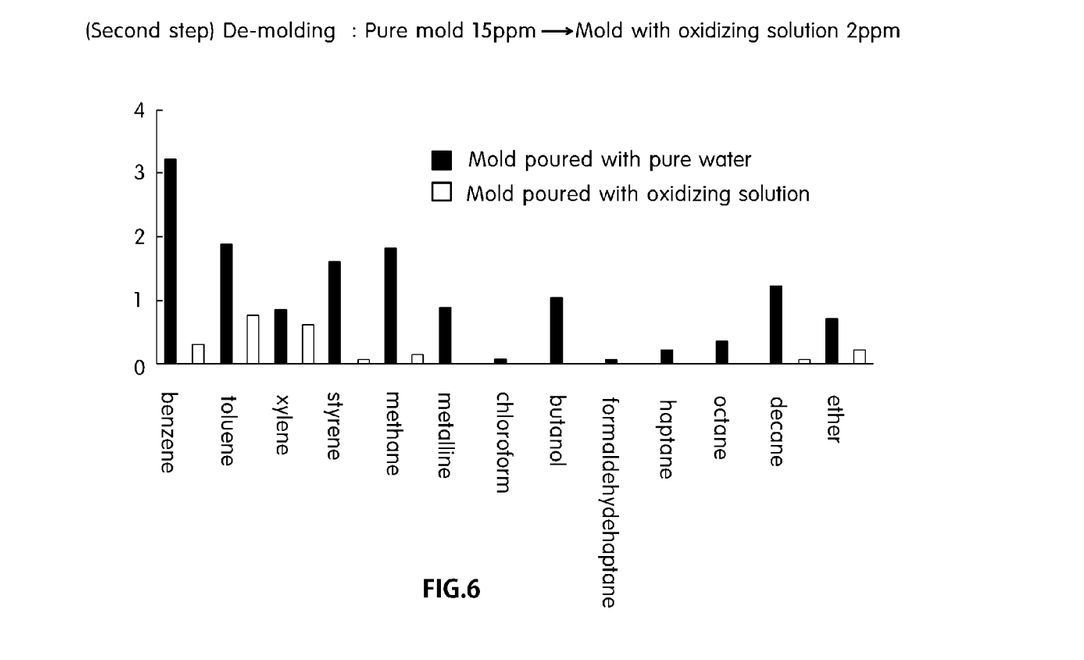

Meanwhile, as shown in FIGS. 5 and 6, it can be seen that the emission of offensive odors and toxic substances was reduced during a pouring/cooling process and a de-molding process using a mold (with an oxidizing solution) prepared by recycling foundry waste treated by advanced oxidation, compared to a conventional mold (with pure water) prepared by pouring pure water in untreated foundry waste. That is, it can be confirmed that when the foundry waste, from which the offensive odors and toxic substances are oxidatively decomposed during the sand reclamation process, is reused to manufacture the mold, the emission of offensive odors and toxic substances is reduced by more than 80% compared to the conventional process.

As described above, according to the advanced oxidation system for the treatment of offensive odors and toxic substances of foundry waste and the treatment method using the same of the present invention, the offensive odors and toxic substances, produced from the foundry waste during the transfer process of the sand reclamation process, is oxidatively decomposed and removed, thereby improving the environmental emissions. As a result, it is possible to reduce the amount of pollutants emitted to the air, thereby preventing civil complaints by the neighboring residential area. Moreover, a separate suppression system is not required, and thus the installation and maintenance costs can be saved.

The invention has been described in detail with reference to exemplary embodiments thereof. However, it will be appreciated by those skilled in the art that changes may be made in these embodiments without departing from the principles and spirit of the invention, the scope of which is defined in the appended claims and their equivalents.

What is claimed is:

1. An advanced oxidation system for the treatment of offensive odors and toxic substances of foundry waste, the system comprising:
    a spray device configured to spray a diluted solution of hydrogen peroxide onto foundry waste;
    a stirring device for mixing configured to mix the foundry waste with the diluted solution of hydrogen peroxide sprayed thereto;
    an ultraviolet irradiation device configured to activate the hydrogen peroxide mixed with the foundry waste to produce radicals;
    a local exhaust system configured to collect dust generated when the foundry waste is mixed with the hydrogen peroxide by the stirring device; and
    a connecting duct connected to a dry suppression system to transfer the collected dust.

2. The system of claim 1, wherein the ultraviolet irradiation device further comprises a plurality of ultraviolet lamps configured to irradiate ultraviolet rays over a mixing vessel of the stirring device and a reflecting means configured to concentrate the ultraviolet rays irradiated from the ultraviolet lamps on the mixing vessel of the stirring device.

3. The system of claim 2, wherein the reflecting means is configured to surround the top and side of the ultraviolet lamps.

4. A method for the treatment of offensive odors and toxic substances of foundry waste using an advanced oxidation system, the method comprising:
    spraying, by a spraying device, a diluted solution of hydrogen peroxide onto foundry waste;
    mixing, by a stirring device, the foundry waste with the diluted solution of hydrogen peroxide sprayed thereto;
    irradiating, by an irradiating device, ultraviolet rays onto the foundry waste mixed with the diluted solution of hydrogen peroxide; and
    collecting by a local exhaust system, dust generated when the foundry waste is mixed with the hydrogen peroxide.

5. The method of claim 4, wherein irradiating the ultraviolet rays further comprises irradiating ultraviolet rays of more than 2 W per 1 kg foundry waste onto the foundry waste for more than 3 minutes.

* * * * *